United States Patent [19]

Kis et al.

[11] Patent Number: 5,281,605

[45] Date of Patent: Jan. 25, 1994

[54] NOVEL XANTHINE DERIVATIVES

[75] Inventors: Zoltan L. Kis, Binningen; John Morley, Allschwil, both of Switzerland

[73] Assignee: Sandoz Ltd., Basel, Switzerland

[21] Appl. No.: 767,290

[22] Filed: Sep. 27, 1991

Related U.S. Application Data

[63] Continuation of Ser. No. 461,146, Jan. 4, 1990, abandoned, which is a continuation of Ser. No. 279,376, Dec. 2, 1988, abandoned, which is a continuation of Ser. No. 89,300, Aug. 25, 1987, abandoned.

[30] Foreign Application Priority Data

Aug. 28, 1986 [GB] United Kingdom ............... 8620825
Jan. 30, 1987 [GB] United Kingdom ............... 8702129
Feb. 13, 1987 [GB] United Kingdom ............... 8703435

[51] Int. Cl.$^5$ .................. A61K 31/52; C07D 473/12; C07D 473/10; C07D 473/08
[52] U.S. Cl. ................. 514/263; 514/265; 544/268; 544/271; 544/272
[58] Field of Search ............ 544/268, 271, 272; 514/263, 265

[56] References Cited

U.S. PATENT DOCUMENTS 3,896,119 7/1975 Klingler .................. 544/272 X
4,400,381 8/1983 Favier et al. ............. 514/265
4,716,166 12/1987 Abou-Gharbia et al. ...... 514/265

FOREIGN PATENT DOCUMENTS 212847 1/1961 Australia.

OTHER PUBLICATIONS

Laboratoire Le Bruns S.A., Chemical Abstracts, vol. 77: 101678x (1972) and Chemical Abstracts Subject Index, vol. 77, Jul.-Dec. 1972, pp. 3327CS-3331CS.
Kremzer, et al., Khimiko Farmatsevticheskii Zhurnal, vol. 15, No. 6, pp. 59-64, Jun. 1981, (English translation, 1982, Plenum Publishing Corp.) Stokin, et al., Chemical Abstracts, vol. 107: 190331g (1987).
Klosa-J. Prakt. Chem. 4, 26, 48-53 (1964).
Gorczyca, Pol. J. Pharmacol Pharm. 27, 305-309 (1975).
Mrozikiewicz, Pl. J. Pharmacol. Pharm., 33, 203-208 (1981).

Primary Examiner—Mark L. Berch
Attorney, Agent, or Firm—Robert S. Honor; Melvyn M. Kassenoff; Thomas O. McGovern

[57] ABSTRACT

A compound of formula I

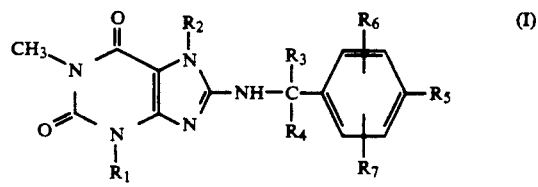

wherein $R_1$ is $C_{1-4}$ alkyl, $C_{3-4}$alkenyl or ($C_{3-5}$cycloalkyl)-methyl, $R_2$ is $C_{1-4}$alkyl, [hydroxy- or ($C_{1-4}$alkoxy)-substituted $C_{1-3}$alkyl]-methyl, ($C_{3-5}$cycloalkyl)-methyl, tetrahydrofuran 2-yl-methyl or 1,3-dioxolan-2-yl-methyl, $R_3$ and $R_4$ are each hydrogen, hydroxymethyl, methoxymethyl or N,N-dimethylcarbamoyloxymethyl, $R_5$ is hydroxy or methoxy, $R_6$ is hydrogen, hydroxy, methoxy or halogen and $R_7$ is in the 2- or 3-position and is hydroxy, methoxy or halogen, or together with $R_5$ is 3,4-methylendioxy, or together with $R_6$ is 2,3-methylenedioxy and their physiologically-hydrolysable and -acceptable esters are useful in the treatment (symptomatic and prophylactic) of obstructive or inflammatory airways disease, in particular asthma, and disease characterised by or having an aetiology comprising morbid eosinophil accumulation or activation, e.g. hypereosinophilia.

13 Claims, No Drawings

NOVEL XANTHINE DERIVATIVES

This is a continuation of application Ser. No. 07/461,146, filed Jan. 4, 1990, abandoned which in turn is a continuation of application Ser. No. 07/279,376, filed Dec. 2, 1988 abandoned, which in turn is a continuation of application Ser. No. 07/089,300, filed Aug. 25, 1987, abandoned.

The present invention relates to novel xanthine derivatives having pharmaceutical utility, processes for their production, pharmaceutical compositions comprising them and their use as pharmaceuticals.

More particularly the present invention provides: a compound of formula I

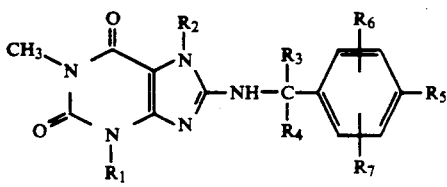

wherein
$R_1$ is $C_{1-4}$alkyl, $C_{3-4}$alkenyl or $(C_{3-5}$cycloalkyl)-methyl, $R_2$ is $C_{1-4}$alkyl, [hydroxy- or $(C_{1-4}$alkoxy)-substituted $C_{1-3}$alkyl]-methyl, $(C_{3-5}$cycloalkyl)-methyl or a group of formula A

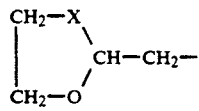

in which X is —$CH_2$— or —O—, $R_3$ and $R_4$ are each hydrogen, hydroxymethyl, methoxymethyl or N,N-dimethylcarbanoyloxymethyl, $R_5$ is hydroxy or methoxy, $R_6$ is hydrogen, hydroxy, methoxy or halogen and $R_7$ is in the 2- or 3-position and is hydroxy, methoxy or halogen, or together with $R_5$ is 3,4-methylenedioxy, or together with $R_6$ is 2,3-methylenedioxy, or physiologically-hydrolysable and -acceptable ester thereof.

Alkyl and alkenyl groups as $R_1$, as well as alkyl groups and the alkoxy and/or alkyl moieties of (hydroxy- and alkoxy-alkyl)methyl groups as $R_2$, may each be branched or straight chain. [Hydroxy- and alkoxy-substituted alkyl]-methyl groups as $R_2$ may be mono-, di- or polysubstituted. Preferably they are monosubstituted. Preferred [hydroxy- and alkoxy-substituted alkyl]-methyl groups as $R_2$ are thus $(C_{1-3}$hydroxyalkyl)-methyl and $(C_{1-4}$alkoxy-$C_{1-3}$alkyl)-methyl.

When $R_1$ is alkenyl, the double bond thereof is preferably separated from the nitrogen atom to which it is attached by at least two carbon atoms. When $R_1$ is cycloalkylmethyl, this is suitably cyclopropylmethyl.

When $R_2$ is a group of formula A this is tetrahydrofuran-2-yl-methyl or 1,3-dioxolan-2-yl-methyl.

By halogen is meant fluorine, chlorine or bromine, especially fluorine or chlorine and, most especially fluorine.

In the compounds of formula I, $R_1$ is suitably methyl. The following significances for $R_2$ to $R_7$ inclusive are preferred, individually, collectively or in any combination or sub-combination:

1. $R_2$ is $C_{1-4}$alkyl, $(C_{1-3}$hydroxyalkyl)-methyl, $(C_{1-4}$alkoxy-$C_{1-3}$alkyl)-methyl, $(C_{3-5}$cycloalkyl)-methyl or a group of formula A. When $R_2$ is $(C_{1-3}$hydroxyalkyl)-methyl this is preferably 2-hydroxyethyl. When $R_2$ is $(C_{1-4}$alkoxy-$C_{1-3}$alkyl)-methyl this is preferably 2-$(C_{1-2}$alkoxy)ethyl, e.g. 2-methoxyethyl.

2. $R_3$ is hydrogen and $R_4$ is hydrogen, hydroxymethyl, methoxymethyl or N,N-dimethylcarbamoyloxymethyl, especially hydroxymethyl or methoxy-methyl.

3. $R_5$ is methoxy.

4a. $R_6$ is hydrogen, hydroxy or methoxy, especially hydrogen.

4b. When $R_6$ is other than hydrogen: $R_6$ is preferably in the 5-position.

5a. $R_7$ is hydroxy or methoxy, especially methoxy.

5b. $R_7$ is in the 3-position.

In one embodiment the present invention provides: a compound of formula I as illustrated above wherein $R_1$ is $C_{1-4}$alkyl, $C_{3-4}$alkenyl or cyclopropylmethyl, $R_2$ is $C_{1-4}$alkyl, [hydroxy- or $(C_{1-4}$alkoxy)-substituted $C_{1-3}$alkyl]-methyl or a group of formula A as defined above, —C($R_3$)$R_4$— is —$CH_2$—, —CH($CH_2$OH)—, —CH($CH_2$OCH$_3$)—, —C($CH_2$OH)$_2$— or —C($CH_2$OCH$_3$)$_2$—, and $R_5$, $R_6$ and $R_7$ have the meanings given for formula I, or physiologically-hydrolysable and -acceptable ester thereof.

By the term "physiologically-hydrolysable and -acceptable ester is meant an ester which is hydrolysable under physiological conditions to yield an acid which is itself physiologically acceptable, i.e. which exhibits no undesirable side effects at desired dosage levels. Such esters may be derived e.g. by acylation of free hydroxy groups in the substituents $R_2$, $R_3$ and $R_4$. Appropriate esters include e.g. those with both mono- and dicarboxylic acids having 2 to 4 carbon atoms, for example esters of compounds of formula I in which $R_2$ is acetoxyethyl and/or $R_4$ is acetoxymethyl, as in the case of the compounds of examples 12, 13 and 16 hereinafter.

Compounds of formula I and esters thereof wherein $R_3$ and $R_4$ are different exist in both S- and R-isomeric form. Similarly compounds of formula I and esters thereof wherein $R_1$ and/or $R_2$ include one or more asymmetric carbon atoms also exhibit optical isomerism. The present invention is to be understood as embracing both individual isomeric forms as well as mixtures, e.g. racaemic and diastereomeric mixtures, thereof unless otherwise specified.

Where the compounds of the invention exist in isomeric form as aforesaid, individual isomers may be obtained in conventional manner, e.g. employing optically active starting materials, e.g. as hereinafter described for examples 22 to 25 or by separation of initially obtained mixtures, e.g. racemic mixtures. In so far as utility in accordance with the present invention resides, in the case of compounds of formula I wherein —C($R_3$)$R_4$— is —CH($CH_2$OH)—, —CH($CH_2$OCH$_3$)— or —CH[$CH_2$O—CO—N(CH$_3$)$_2$]— and esters thereof, primarily in those compounds and esters wherein the grouping —C($R_3$)$R_4$— has the R-configuration, the R-isomers in pure or substantially pure form, or mixtures, e.g. racemic mixtures, comprising the R-isomer will be preferred.

Accordingly in a specific aspect the present invention provides: a compound of formula I as illustrated above wherein $R_1$, $R_2$, $R_5$, $R_6$ and $R_7$ have the meanings hereinbefore given and —C($R_3$)$R_4$— is (R) —CH(CH$_2$OH)—, (R) —CH(CH$_2$OCH$_3$)— or (R) —CHECH$_2$O—CO—N(CH$_3$)$_2$]—, or a physiologically- hydrolysable and -acceptable ester thereof.

In addition to the foregoing the present invention also provides: a process for the production of compounds of formula I and esters thereof as defined above, which process comprises:

a) for the production of a compound of formual I having a free hydroxy group, deprotecting a hydroxy-protected derivative thereof;

b) for the production of a compound of formula I, reacting a compound of formula II

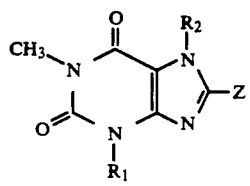

wherein $R_1$ and $R_2$ have the meanings given above and Z is a leaving group, with a compound of formula III

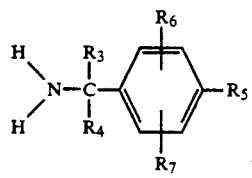

wherein $R_3$ to $R_7$ have the meanings given above, whereby any hydroxy group present in the compound of formula II or III may be in free or protected form and, when required, carrying out process step a), c) for the production of a physiologically-hydrolysable and -acceptable ester of a compound of formula I, esterifying a compound of formula I having a free hydroxy group, any hydroxy group present which is not to be esterified being, when required, in protected form, employing an appropriate acid or derivative thereof and, when required, carrying out process step a); and, if desired, d) separating optically active isomers from any mixture of such isomers obtained in accordance with steps a), b) or c).

Process step a) may be carried out in accordance with means known in the art for the removal of hydroxy protecting groups, e.g. for the deprotection of benzyl-protected hydroxy groups, by ether cleavage, for example via hydrogenation in the presence of a Pd/charcoal catalyst.

Process step b) above can be carried out in accordance with means generally known in the art, for example by reaction of a compound of formula II with a compound of formula III at a temperature of from ca. 20 to 180° C. in the presence of an inert solvent or diluent, suitably in the presence of an acid binding agent such as triethylamine. Suitable leaving groups as Z include e.g. halogen atoms, in particular chlorine or bromine atoms.

Process step c) is also conventional and may be performed e.g. by esterification employing an appropriate acid halide or acid anhydride, suitably in the presence of an acid binding agent such as pyridine, e.g. at a temperature of from 20 to 100 ° C.

Where hydroxy groups are present in the starting materials of formula I, II or III which might otherwise be susceptible to undesired side reaction, these may be in protected form. Suitable hydroxy-protecting groups include any of those known and commonly employed in the art including e.g. benzyl. Such protecting groups are the removed subsequent to the main defined reaction in accordance with process step a).

Use of optically active starting materials for process steps a) through c) will lead directly to optically active compounds of formula I or esters thereof. Alternatively, individual optically active isomers may be recovered from initially obtained mixtures, e.g. racemic or diastereomeric mixtures, thereof in accordance with process step d) and employing any of the techniques known and commonly practiced in the art.

The starting materials of formula II and III are known or may be produced analogously to known techniques, in the case of compounds of formula II for example, by 7N-alkylation of theophylline, or analogues thereof wherein the substituent at the 4-position is other than methyl, so as to introduce the desired group $R_2$.

The following examples are illustrative of the processes of the present invention:

EXAMPLE 1

8-[α-hydroxymethyl-(3,4-dimethoxy-henzylamino)]-caffeine [formula I: $R_1=R_2=CH_3$; $R_3=H$; $R_4=HOCH_2$-; $R_5=CH_3O$—; $R_6=H$; $R_7=(3) CH_3O$—]

5 g 8-chlorocaffeine and 5.6 g a-hydroxymethyl-3,4-dimethoxybenzylanine are dissolved, together with 8 ml triethylamine in 200 ml ethanol. The reaction mixture is heated in an oil bath at 170 ° C., with stirring, in an autoclave for 76 hours, evaporated and the residue crystallised from ethanol. The pure title compound is obtained following further washing with water: m.p. 217°-218° C.

The following compounds of formula Ia may be obtained analogously:

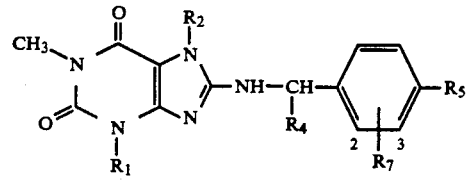

| EXAMPLE | $R_1$ | $R_2$ | $R_4$ | $R_5$ | $R_7$ | m.p. (°C.) |
|---|---|---|---|---|---|---|
| 2 | CH$_3$— | CH$_3$— | H | CH$_3$O— | (3)CH$_3$O— | 237–239 |
| 3 | CH$_3$— | CH$_3$O—(CH$_2$)$_2$— | H | CH$_3$O— | (2)CH$_3$O— | 147–149 |
| 4 | CH$_2$=CH—CH$_2$— | CH$_3$O—(CH$_2$)$_2$— | H | CH$_3$O— | (3)CH$_3$O— | 116–117 |
| 5 | CH$_2$=CH—CH$_2$— | HO—(CH$_2$)$_2$— | H | CH$_3$O— | (3)CH$_3$O— | 163–164 |
| 6 | CH$_3$— | CH$_3$O—(CH$_2$)$_2$— | H | CH$_3$O— | (3)CH$_3$O— | 154–154.5 |
| 7 | CH$_3$— | CH$_3$O—(CH$_2$)$_2$— | HO—CH$_2$— | CH$_3$O— | (3)CH$_3$O— | 139–140 |

-continued

| EXAMPLE | R₁ | R₂ | R₄ | R₅ | R₇ | m.p. (°C.) |
|---|---|---|---|---|---|---|
| 8 | CH₃— | HO—(CH₂)₂— | HO—CH₂— | CH₃O— | (3)CH₃O— | 192–193 |
| 9 | CH₃— | HO—(CH₂)₂— | H | CH₃O— | (3)CH₃O— | 174–175 |
| 10 | ▷—CH₂— | CH₃O—(CH₂)₂— | H | CH₃O— | (3)CH₃O— | 130–131 |
| 11 | CH₃— | CH₃O—(CH₂)₂— | CH₃O—CH₂— | CH₃O— | (3)CH₃O— | 106–109 |
| 12 | CH₃— | CH₃O—(CH₂)₂— | CH₃—CO—O—CH₂— | CH₃O— | (3)CH₃O— | 140.5–151 |
| 13 | CH₂=CH—CH₂— | [O,O]>—CH₂— | CH₃—CO—O—CH₂— | CH₃O— | (3)CH₃O— | 113–114 |
| 14 | CH₂=CH—CH₂— | [O,O]>—CH₂— | H | CH₃O— | (3)CH₃O— | 126–128 |
| 15 | CH₃— | [O,O]>—CH₂— | H | CH₃O— | (3)CH₃O— | 200–201 |
| 16 | CH₃— | CH₃—CO—O—(CH₂)₂— | H | CH₃O— | (3)CH₃O— | 162.5–163 |
| 17 | ▷—CH₂— | [O,O]>—CH₂— | H | CH₃O— | (3)CH₃O— | 139.5–141 |
| 18 | CH₂=CH—CH₂— | [O,O]>—CH₂— | HOCH₂— | CH₃O— | (3)CH₃O— | 113–115 |
| 19 | CH₃— | HO—(CH₂)₂— | CH₃O—CH₂— | CH₃O— | (3)CH₃O— | 147–149 |
| 20 | CH₃— | ▷—CH₂— | HOCH₂— | CH₃O— | (3)CH₃O— | ① |
| 21 | CH₃— | CH₃O—(CH₂)₂— | (CH₃)₂N—CO—O—CH₂— | CH₃O— | (3)CH₃O— | ② |

The compounds of examples 12, 13 and 16 above are prepared by acetylation of the compounds of examples 7, 18 and 9 respectively employing acetic acid anhydride. The reaction is performed in conventional manner in the presence of pyridine and CH₂Cl₂ as solvent at a temperature of ca. 20° C.

The compound of example 19 is prepared by debenzylation of the corresponding compound in which R₂ is in O-benzyl protected form, this being in turn produced anlogously to example 1 employing 7-benzyloxy-ethyl-bromotheophylline in place of 8-chlorocaffeine. Debenzylation is effected by hydrogenation at 1 atm, and 20° C. in ethanol emplyoing a 10% Pd/C catalyst.

① m.p. for the R-isomer = 165°–166° C., $[\alpha]_D^{20} = +30°$ (c = 1,1 in CH₃OH).

② m.p. for the R-isomer = 54°–56° C., $[\alpha]_D^{20} = +23°$ (c = 1.1 in CH₂Cl₂).

The R-isomer product of example 20 is obtained employing R-(α-hydroxyimethyl-3,4-dimethoxy benzyl)amine as starting material hereinafter described forexample 22. The R-isomer product of example 21 is obtained from the product of example 22 hereinafter by reaction with dimethylcarbonylchloride in dioxane as solvent in the presence of sodium hydride at a temperature of ca. 20° C.

The following compounds of formula Ib are prepared analogously to example 1, in the case of the compounds of examples 22 and 23, employing the indicated optically active starting materials, in the case of the comounds of examples 24 and 25, by phase-transfer alkylation of the products of examples 22 and 23 as described.

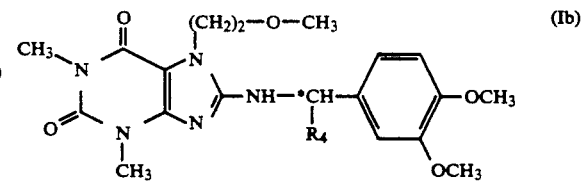

(Ib)

| EXAMPLE | R₄ | CONFIGURATION AT * | m.p. (°C.) | $[\alpha]_D^{20}$ (c = in CH₂Cl₂) |
|---|---|---|---|---|
| 22 | HOCH₂— | R | 129–130 | +15.3 (1) |
| 23 | HOCH₂— | S | 129–130 | −16.0 (1 |
| 24 | CH₃O—CH₂— | R | 104–105 | +55.7 (1.05) |
| 25 | CH₃O—CH₂— | S | 104–105 | −56.5 (1.01) |

Starting materials for examples 22 and 23
8-Bromo-(2-methoxyethyl)-theophylline with:

22. R-(α-hydroxymethyl-3,4-dimethoxybenzyl)amine,
23. S-(α-hydroxymethyl-3,4-dimethoxybenzyl)amine.

Preparation of the products of examples 24 and 25

5 g NAOH is dissolved in 10 ml water and supplemented at ambient temperature with 0.7 ml benzyltrimethylamonium hydroxide. 1.1 g of product compound from example 22 or 23 is dissolved in 15 ml dichloromethane to provide the second phase. The two phases are mixed with vigorous stirring and 1 ml dimethylsulfate is added drop-wise over 8 hrs. Stirring is continued for a further 20 hrs., the resulting mixture diluted with dichloromethane, separated and the organic phase- extracted with diluted tartaric acid, washed with water and dried over Na2SO4- The obtained product is then purified chromatographically employing silica gel with ethylacetate/1% methanol as eluant.

In relation to the present invention the isomers of examples 22 and 24 above are preferred to the isomers of examples 23 and 25 respectively as exhibiting a higher level of activity as evidenced in animal models a hereinafter described.

Compounds of formula I and their esters as hereinbefore defined posess bronchodilator and anti-asthmatic activity as may be shown in standard test models, e.g. as follows:

EXAMPLE A

BRONCHODILATOR ACTIVITY

1. Bronchospasmolytic activity in vitro 1.1. Isolated guinea-pig trachea:

The trachea is excised from freshly sacrificed guinea-pigs and transected in the transverse plane to give rings of tissue of ca. 2 mm. Individual rings are mounted vertically on stainless steel supports, one of which is fixed at the base of an organ bath, the other being attached to a tension transducer. The rings are bathed in modified Tyrode solution at 37° C. and gassed with $O_2/CO_2$ (95:5, v/v). Rings prepared in this manner, preloaded with 1 g, generate spontaneous tone and, after a period of equilibration, relax on addition of spasmolytic drugs. Tension can be enhanced by addition of carbachol ($10^{-6}M$) or histamine ($10^{-4}M$). To ascertain spasmolytic activity, test substances are dissolved in physiological saline and added in increasing quantities to the organ bath at 5 min. intervals to provide a cumulative concentration-effect curve.

In the above test model compounds and esters of the invention produce concentration-related relaxation of guinea-pig tracheal ring preparations irrespective of the contractile agency at concentrations of from about $5 \times 10^{-7}$ to about $10^{-5}M$ with respect to basal tone, from about $1,5 \times 10^{-5}$ to about $10^{-4}M$ in the presence of carbachol, and from about $10^{-7}$ to about $10^{-5}$ in the presence of histamine.

1.2. Isolated human bronchus:

Rings of bronchus (ca. 2 mm depth) are dissected from samples of human lung, resected from patients with lung carcinoma but grossly free of disease. Activity is determined employing the methodology of example A.1.1.

In the above test model compounds and esters of the invention produce contraction-related relaxation of human bronchus ring preparations irrespective of the contractile agency at dosages of from about $10^{-6}$ to about $10^{-4}M$.

2. Bronchodilator activity in vivo 2.1. Inhibition of bronchospasm:

Guinea pigs are anaesthetised with pentobarbital (30 mg/kg i.p.) and phenobarbital (100 mg/kg i.p.) and ventilated via a tracheal cannula (10 ml/kg, 1 Hz). Ventilation is monitored either by a pressure transducer measuring air-flow (Konzett-Rossler method), or by a Fleisch flow transducer in line with the inspiratory circuit. When making measurements of flow, coincident pressure changes in the thorax are monitored directly via an intrathoracic trochar, permitting display of differential pressure relative to the trachea. From this information resistance and compliance are calculated at each inspiration.

Intravenous injection of bombesin (ca. 500 μg/kg) as a bolus, induces increased airways resistance Wilich is sustained over a period of several minutes. Capacity of test-substance to reverse response when administered i.v. at the height of bombesin-induced bronchospasm serves as a measure of efficacy in reversing established bronchospasm.

In the above test model, compounds and esters of the invention are found to effect dose related abrogation of bronchospasm at dosages of from about 0.01 to about 1.0 mg/kg i.v.

2.2. Inhibition of bronchoconstriction following pulmonary administration:

Conscious guinea-pigs are subjected to inhalation of test substance or placebo (vehicle) 10 mins. prior to explosure to a 0.3% mist of acetylcholine. Test substance is administered as a mist generated from aerosol preparations at concentrations of from 1 mg/ml to 0.001 mg/ml. Prolongation of time prior to collapse in treated groups as compared with placebo groups is taken as a measure of bronchodilator efficacy.

In the above test model, detectable protection against bronchospasm is evident employing compounds and esters of the invention on introduction into the exposure chamber in 1ml amounts at the above indicated concentrations.

EXAMPLE B

SUPPRESSION OF AIRWAYS HYPERREACTIVITY

1. Sensitised Animals

Guinea pigs are anaesthetised and airways resistance and compliance recorded as described under example A.2.1. above. Intravenous injection of histcynine (1–1.8 μg/kg) is used to define airways sensitivity. Allergic reaction is initiated by i.v. injection of preformed immune complexes (bovine γ-globulin/anti-bovine γ-globulin), using a dose that is scarcely sufficient to induce bronchospasm at the first injection. This dose of immune complexes is repeated at regular (10 min.) intervals.

Following the last dose of immune complexes, the dose-effect relationship to histarnine is re-defined. In animals so treated, induction of airways hyperreactivity is consistently observed.

On advance administration of compounds and esters of the invention at dosages of from about 0.03 to about 3.0 mg/kg i.v., suppression of induced airways resistance is observed as compared with untreated controls.

2 PAF-Treated Animals

Guinea-pigs are anaesthetised and prepared for recording of lung function as described under example A.2.1. above. Intravenous injection of histamine establishes airways sensitivity to spasmogens. Following infusion of PAF (platelet activating factor) over 1hr. (total dose=600 ng/kg), repeated injection of histamine reveals development of airways hyperreactivity, which can conveniently be expressed as the paired difference between the response amplitude before and after PAF exposure.

On administration of compounds and esters of the invention by infusion during PAF exposure at dosages of from aout 0.1 to about 20 mg/kg i.v., suppression of airways hyperreactivity induction is observed.

EXAMPLE C

INFLUENCE ON EOSINOPHIL ACCUMULATION

Effect of test-substance is conveniently determined by measurement of influence on PAF-induced eosinophil accumulation in the guinea-pig peritoneal cavity in vivo. In the guinea-pig, there is a substantial (up to 40%) resident population of eosinophils in the peritoneal cavity and eosinophil accumulation in the peritoneal cavity relative to control animals ca. 24-48 hrs. following injection of PAF i.p. at dosages of ca. 10 $\mu$g/kg serves to establish the influence of test substance on eosinophil accumulation.

To establish eosinophil accumulation, test animals receive 10 $\mu$g/kg PAF i.p., 2 days prior to sacrifice. Smears from the peritoneal cavity are prepared employing Leishman's Stain after fixation with 95% methanol. At least 500 white cells are differentiated for each estimation. Test substance is administered s.c. via a minipump for four days prior to sacrifice.

On administration of compounds andesters of the invention in the above test model at dosage rates of from about 0.1 to about 10.0 mg/kg/day s.c., for a number of days prior to sacrifice and employing non-PAF-treated animals, decrease in resident eosinophil population may be observed as compared with untreated controls.

Having regard to their bronchospasmolytic activity as evidenced in test methods as described in example A above, compounds and esters of the invention are useful as bronchodilators, e.g. for the treatment, e.g. symptomatic treatment of obstructive or inflammatory airways disease, for example asthma, pneumoconiosis or bronchitis. Having regard to their activity a) in inhibiting acute response in hypersensitive subjects following allergen or other challenge elliciting hypersensitivity reaction (e.g. following induction of hyperreactivity and airways obstruction via PAF challenge), b) in suppressing development of airways hyperreactivity subsequent to challenge as under a), and c) in diminishing basal, or on-going, airways hyperreactivity, as evidenced in test methods as described in example B above, compounds and esters of the invention are useful for the prophylactic treatment of obstructive or inflammatory airways disease, for example the prophylactic treatment of pneumoconiosis and, in particular, asthma.

[For further discussion of the relevance of a), b) and c) above and their relationship to prophylactic utility in treating inflammatory airways disease, see e.g.: Altounyan, Clin. Allergy (supp.) 10, 481-489 (1980); Morley et al., Lancet ii, 1142-1144 (1984); Mazzoni et al., J. Physiol., 365, 107 P (1985); Traietti et al., Respiration, 46, 62-63 (1984); Taytard et al., Am. Rev. Repiratory Disease, 134, 983-985 (1986); Szezeklik et al., Thrombosis and Hematosis, 56, 283-287 (1986); Basran et al., Clin Allergy, 14, 75-79 (1984); Karlsson et al., Brit. J. Clin. Pharmacol. 27, 371-374(1985); and Mazzoni et al., Brit. J. Pharmacol., 86, 571P (1985)].

As bronchodilator agents, compounds and esters of the invention may be used to abort or restrict bronchoconstrictor attack consequential to obstructive or inflammatory airways disease, e.g. asthma (symptomatic treatment). As prophylactic agents, compounds and esters of the invention may, by continued administration, be used to provide advance protection against recurrence of bronchoconstrictor attack consequential to obstructive or inflammatory airways disease, e.g. asthma, or for the control, restriction or reversal of basal status of such disease, e.g. for the control, restriction or reversal of basal causes of asthma and asthma attack. The words "treatment" and "treating" as used throughout the present specification and claims are accordingly to be understood as including prophylactic as well as symptomatic modes, unless otherwise specified.

In accordance with the foregoing the present invention accordingly also provides:

I. A method for the treatment of obstructive or inflammatory airways disease in a subject in need thereof, which method comprises administering to said subject an effective amount of a compound of formula I as hereinbefore defined or a physiologically-hydrolisable and -acceptable ester thereof for example;

Ia. A method of effecting bronchodilatation in a subject in need thereof (for example a subject exhibiting obstructive or inflammatory airways disease or airways obstruction, including chronic or acute obstruction, for example as occurring in the symptomatology of diseases, disorders or conditions as herein set forth), which method comprises administering to said subject a bronchodilatorily effective amount of a compound of formula I as hereinbefore defined or a physiologically-hydrolysable and -acceptable ester thereof or Ib. A method for the prophylactic treatment of obstructive or, more particularly, inflammatory airways disease (e.g. for advance protective treatment against acute airways obstruction, for example bronchospasm, e.g. as occurring in the symptomatology of diseases, disorders or conditions as herein set forth) in a subject in need thereof, which method comprises administering to said subject a prophylactically effective amount of a compound of formula I as hereinbefore defined or a physiologically-hydrolysable and -acceptable ester thereof.

In the alternative the present invention provides:

II. A compound of formula I as hereinbefore defined or a physiologically-hydrolysable and -acceptable ester thereof for use as a pharmaceutical, for example for use in the treatment of obstructive or inflammatory airways disease, e.g. for use in a method as defined under I, Ia or Ib above.

The method of the present invention as defined under I to Ib above is, in particular, applicable to the treatment of asthma of whatever type or genesis. It is applicable to both intrinsic and, especially, extrinsic asthma. It is especially applicable to the treatment of allergic asthma, whether atopic, (i.e. IgE-mediated) or non-atopic, as well as e.g. bronchitic asthma, thymic asthma, excercise induced asthma, occupational asthma, asthma induced following bacterial infection and other non-allergic asthmas. Treatment of asthma is also to be understood as embracing treatment of subjects, e.g. of less th-an 4or 5 years of age, exhibiting wheezing symptoms, in particular at night, and diagnosed or diagnosable as "wheezy infants", an established patient category of major medical concern and now more correctly identified as incipient or early-phase asthmatics. (For convenience of definition this particular asthmatic condition is referred to hereinafter as "wheezy-infant syndrome").

In a series of particular embodiments the present invention thus provides for treatment of asthma, in particular allergic asthma (for example allergic atopic asthma), exercise induced asthma and wheezy-infant syndrome, including symptomatic treatment of asthma (e.g. bronchodilator treatment of asthma exacerbation or attack) as well as prophylactic treatment of asthma (e.g. prophylactic treatment of asthma exacerbation or attack), comprising use of or administration of a compound of formula I as hereinbefore defined or a physiologically-hydrolysable and -acceptable ester thereof.

The method of the present invention as defined under I to Ib above is also applicable to the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

In a further series of particular embodiments the present invention thus also provides for the treatment of pneumoconiosis, in particular byssinosis, including symptomatic treatment of airways obstruction (e.g. bronchodilator treatment of acute or chronic airways obstruction, e.g. dyspnea or bronchospasm) attributable thereto, as well as prophylactic treatment of airways obstruction (e.g. advance protective treatment of acute airways obstruction, e.g. bronchospasm) attributable thereto, comprising use or administration of a compound of formula I as hereinbefore defined or a physiologically-hydrolysable and -acceptable ester thereof.

The method of the present invention as defined under I or, especially, Ia above, is also applicable to the treatment of bronchitis or, more especially, the treatment of chronic or acute airways obstruction, for example, dyspnea, associated therewith. In this respect the present invention is applicable to the treatment of bronchitis of whatever type or genesis, including, for example, acute bronchitis, arachidic bronchitis, catarrhal bronchitis, chronic bronchitis, croupous bronchitis, phthinoid bronchitis and so forth.

In a further series of particular embodiments the present invention accordingly provides for the treatment of bronchitis or, more especially, the symptomatic treatment of airways obstruction (e.g. bronchodilator treatment of acute or chronic airways obstruction, e.g. dyspnea) attributable thereto, comprising use or administration of a compound of formula I as hereinbefore defined or a physiologically-hydrolysable and -acceptable ester thereof.

Having regard to activity of compounds and esters of the invention in suppressing eosinophil accumulation as may be demonstrated in test models such as described in example C above the present invention also provides:

III A method for the suppression of eosinophil accumulation and/or activation, e.g. for the treatment of disease characterised by or having an aetiology comprising morbid eosinophil accumulation and/or activation, in a subject in need of such treatment which method comprises administering to said subject an effective-amount of a compound of formula I as hereinbefore defined or a physiologically-hydrolysable and -acceptable ester thereof;

or, in the alternative:

IV A compound of formula I as hereinbefore defined or a physiologically-hydrolysable and -acceptable ester thereof for use in a method as defined under III above.

Diseases as defined under III above include, in particular, hypereosinophilia and the eosinophil related disorders.

Hypereosinophilia is a distinct condition or status of varied aetiology characterised by chronic, morbid eosinophil presence in the body tissues generally. The eosinophil-related disorders comprise a distinct and extensively documented indication group, commonly occurring concomitant to another, primary disease or condition. [For more detailed discussion see e.g.: Schatz et al., Medical Clinics of North America, 65, (5), 1055–1071 (1981) and Ottesen et al., "Allergy, Principles and Practice", Eds.E. Middleton, C. Reed and S. Ellis, 584–632, (1987)]. The group includes eosinophil-related disorders of the airways (involving morbid eosinophilic infiltration of pulmonary tissues) as well as of other organs and tissues including, for example, the skin, eye, nasal passages and the gastrointestinal and urinary tracts.

Eosinopil-related disorders to which the present invention is applicable include those concomitant to atopy or atopic reactions in general (e.g. atopic conditions such as rhinitis, conjunctivitis etc . . . as set forth below) as well as non-atopic eosinophil-related disorders.

Disorders of the airways to which the present invention is applicable include hypereosinophilia as well as, for example, eosinophil-related disorders of the airways consequential or concomitant to Lbffler's syndrome, eosinophilic pneumonia, parasitic (in particular metazoan) infestation (including tropical eosinophilia), bronchopulmonary aspergillosis, polyarteritis nodosa (including Churg-Strauss syndrome) as well as eosinophil-related disorders affecting the airways occasioned by drug-reaction.

Other eosinophil-related disorders to which the present invention is applicable include eosinophilia consequential or concomitant to eosinophilic gastroenteritis, Heiner's syndrome, atopic dermatitis, urticaria or angioderma (allergic, recurrent or prolonged), ichthyosis, exfoliative dermatitis or pityriasisrubra, urticaria pigmentosa or mastocytoma, toxic epidermal necrolysis (drug related), dertnatitis herpetiformis, allergic rhinitis, hyperplastic sinusitis, interstitial nephritis (drug related), interstitial cystitis, choleostatic hepatotoxicity (drug related), allergic conjunctivitis, vernal conjunctivitis, eosinophilic fascitis, hypersensitivity angiitis, serous myocarditis or endornyocardial fibrosis, Wiscott-Aldrich syndrome, selective IgA deficiency with atopy, eosinophilic leukemia and eosinophilic granuloma.

As will be appreciated, the present invention is directed primarily to the treatment-of hypereosinophilia or eosinophilrelated disorders as such. Where, however, eosinophil-related disorders are concomitant to atopy, for example to any of the atopic diseases or conditions specifically recited above including atopic or allergic forms of dermatitis, urticaria, angioderma, rhinitis, conjunctivitis and gastrointestinal allergies, the present invention may equally be applicable to the treatment of eosinophil-related disorder as an integral or basal component thereof. The present invention thus also provides means for the treatment (e.g. symptomatic or prophylactic treatment) of atopy, including each of the said recited atopic diseases or conditions, as such. In treating eosinophil-related disorders concomitant to non-atopic diseases or conditions on the other hand, the compound and esters of the invention will more commonly be administered together with other medication for treatment of the disease or condition with which eosinophilia is associated. Thus in the treatment of eosinophilia consequential to parasitic infection, use will generally be in conjunction with other, anti-parasitic drug therapy.

Where compounds and esters of the invention are employed in accordance with the method of the invention for the treatment of eosinophil-related disorders of the airways, e.g. for the treatment of hypereosinophilia as it affects the lungs or for the treatment of pulmonary eosinophilia associated with eosinophilic pneumonia, and the disorder is accompanied by symptoms of airways obstruction, they may be employed either as symptomatic or prophylactic therapy, e.g. either to alleviate or abort, or to provide advance protection against recurrence of, obstruction. More commonly however compounds and esters of the invention will be employed symptomatically, e.g. as a means for the treatment of hypereosinophilia or eosinophil-related disorder, i.e. in accordance with methods defined under III above.

In a further series of particular embodiments the present invention thus also provides:

i) for the treatment of hypereosinophilia and of eosinophil related disorders, including treatment in accordance with the methods defined under III above, including, in the case of eosinophil-related disorders of the airways associated with airways obstruction, symptomatic treatment of airways obstruction (e.g. bronchodilator treatment of acute or chronic airways obstruction, e.g. dyspnea or bronchospasm) and prophylactic treatment of airways obstruction (e.g. advance protective treatment of acute airways obstruction, e.g. bronchospasm) attributable thereto, comprising use or administration of a compound of formula I as hereinbefore defined or a physiologically-hydrolysable and -acceptable ester thereof; as well as ii) for the treatment of atopy, for example for the treatment of any of the atopic diseases or conditions causal to or associated with eosinophil-related disorder as hereinbefore set forth, comprising use or administration of a compound of fomula I as hereinbefore defined or a physiologically hydrolysable and -acceptable ester thereof.

Dosages required for use in accordance with the present invention will of course vary depending on e.g. the particular compound or ester of the invention employed, the mode of administration, the particular condition to be treated and the effect desired. In general however, satisfactory results are obtained on administration at a daily dosage of from about 0.01 to about 10 mg/kg animal body weight, e.g. administered i.v..For larger mwnals an indicated daily dosage for oral administration in particular for the symptomatic and/or prophylactic treatment of obstructive or inflammatory airways disease, for example asthma, is in the range of from about 50 to about 500 mg per day, in particular from about 100–300 mg per day, conveniently administered in divided doses 2 to 4×/day or in sustained-release form. Suitable unit dosage forms for oral administration accordingly comprise from about 12 to about 500, in particular from about 25 to about 150 or 300 mg compound or ester of the invention, together with a pharmaceutically acceptable diluent.or carrier therefor.

The compounds and esters of the invention may be ackninistered in similar manner to known standards, e.g. theophylline, for use in the recited indications, e.g. orally in oral unit dosage form, e.g. in the form of tablets or capsules. They exhibit a low degree of side effects such as psychostimulation as compared with other clinically employed xanthine bronchodilator drugsubstances, for example theophylline or aminophylline.

In accordance with the foregoing the present invention also provides: a pharmaceutical composition comprising a compound of formula I as hereinbefore defined or a physiologically-hydrolysable and -acceptable ester thereof, together with a pharinaceutically acceptable diluent carrier therefor.

As previously indicated dosages of compound or ester of the invention employed in practising the various methods of the present invention will in particular depend on the particular compound or ester chosen and its relative potency of activity. In this regard, EC50 and ED50 values for the preferred compound of the invention in racemic form (the product of example 7) and in R-isomeric form (the product of example 22) established in one series of trials in accordance with examples A.l.l., A.1.2. and A.2.1. as follows.

| TEST METHOD - EXAMPLE | COMPOUND OF EXAMPLE | $EC_{50}/ED_{50}$ |
| --- | --- | --- |
| A.1.1. | | |
| BASAL TONE | | $EC_{50} = 8.6 \times 10^{-7}$ M |
| CARBACHOL | 22. | $EC_{50} = 1.9 \times 10^{-5}$ M |
| HISTAMINE | | $EC_{50} = 1.7 \times 10^{-7}$ M |
| A.1.2. | 7 | $EC_{50} = 1.2 \times 10^{-6}$ M |
| A.2.1. | 22 | $ED_{50}$ between 0.03 and 0.09 mg/kg i.v. |

In the method of example B.2, 50% inhibition of hyperreactivity assessed as the % reduction of the incremental increase in response to constant dose histamine after PAF infusion is observed employing the compound of example 8 at dosages of from ca. 0.5 to 1.0 mg/kg i.v. administered as a bolus or by infusion over 1 hr.

We claim:

1. A compound of formula I

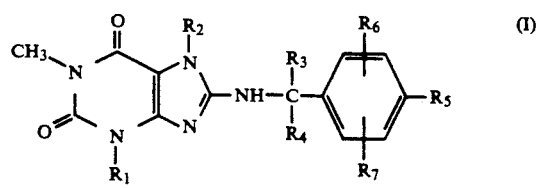

wherein
$R_1$ is $C_{1-4}$alkyl, $C_{3-4}$alkenyl or ($C_{3-5}$cycloalkyl)-methyl,
$R_2$ is $C_{1-4}$alkyl, [hydroxy- or ($C_{1-4}$alkoxy)-substituted $C_{1-3}$alkyl]-methyl, ($C_{3-5}$cycloalkyl)-methyl or a group of formula A.

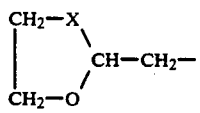 (A)

in which X is —CH$_2$— or —O—,

R$_3$ is hydrogen and R$_4$ is hydroxymethyl, methoxymethyl or N,N-dimethylcarbamoyloxymethyl, R$_5$ is hydroxy or methoxy, R$_6$ is hydrogen, hydroxy, methoxy or halogen and R$_7$ is in the 2- or 3-position and is hydroxy, methoxy or halogen, or together with R$_5$ is 3,4-methylenedioxy, or together with R$_6$ is 2,3-methylenedioxy or physiologically-hydrolysable and -acceptable carboxylic acid ester thereof.

2. A compound of formula I

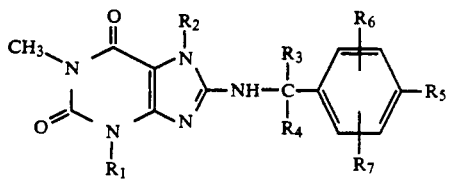 (I)

where

R$_1$ is C$_{1-4}$alkyl, C$_{3-4}$alkenyl, or (C$_{3-5}$cycloalkyl)-methyl,

R$_2$ is C$_{1-4}$alkyl, [mono hydroxy- or mono(C$_{1-4}$alkoxy)-substituted C$_{1-3}$alkyl]-methyl, (C$_{3-5}$cycloalkyl)-methyl or a group of formula A

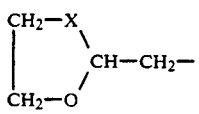 (A)

in which

X is —CH$_2$— or —O—,

R$_3$ is hydrogen, and

R$_4$ is hydroxymethyl, methoxyethyl, or N,N0dimethylcarbamoyloxymethyl,

R$_5$ is hydroxy or methoxy,

R$_6$ is hydrogen, hydroxy, methoxy or halogen and

R$_7$ is in the 2- or 3-position and is hydroxy, methoxy or halogen, or together with R$_5$ is 3,4-methylenedioxy, or together with R$_6$ is 2,3-methylenedioxy, or physiologically-hydrolysable and -acceptable carboxylic acid ester thereof.

3. A compound according to claim 2 wherein R$_1$ is CH$_3$-, R$_2$ is CH$_3$O-(CH$_2$)$_2$—, R$_3$ is hydrogen, R$_4$ is HO—CH$_2$—, R$_5$ is CH$_3$O—, R$_6$ ish ydrogen and R$_7$ is CH$_3$O— in the 3-position.

4. A compound according to claim 2 wherein R$_1$ is CH$_3$—, R$_2$ is CH$_3$O—(CH$_2$)$_2$—, R$_3$ is hydrogen, R$_4$ is CH$_3$O—CH$_2$—, R$_5$ is CH$_3$O—, R$_6$ is hydrogen and R$_7$ is CH$_3$O— in the 3-position.

5. A compound according to claim 2 wherein the group

—C(R$_3$)R$_4$— is (R) —CH(CH$_2$OH)—, (R) —CH(CH$_2$OCH$_3$)— or (R) —CH[CH$_2$—O—CO—N(CH$_3$)$_2$]- or physiologically-hydrolysable and —acceptable carboxylic acid ester thereof.

6. A compound according to claim 3 wherein the group —C(R$_3$)R$_4$— is (R) —CH(CH$_2$OH)—.

7. A compound according to claim 4 wherein the group —C(R$_3$)R$_4$— is (R) —CH(CH$_2$OCH$_3$)—.

8. A pharmaceutical composition comprising a therapeutically effective amount a compound or ester as claimed in claim 1 together with a pharmaceutically acceptable diluent or carrier therefor.

9. A method for the treatment of obstructive or inflammatory airways disease or for the suppression of eosinophil accumulation or activation or for the treatment of atopy, causal to or associated with eosinophil related disorders of the airways in a subject in need thereof, which method comprises administering to said subject an effective amount of a compound of formula I as defined in claim 1 or physiologically-hydrolysable and -acceptable carboxylic ester thereof.

10. A method according to claim 9 for the treatment of asthma.

11. A compound according to claim 1 in which R$_4$ is a C$_{2-4}$ mono-or di-carboxylic acid ester of hydroxymethyl.

12. A compound or ester according to claim 2 wherein R$_3$ is hydrogen, R$_5$ is CH$_3$O—, R$_6$ is hydrogen and R$_7$ is CH$_3$O— in the 3-position and

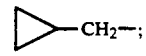

or e) R$_1$ is CH$_3$—, R$_4$ is CH$_3$O—CH$_2$— and R$_2$ is HO—(CH$_2$)$_2$—; or f) R$_1$ is CH$_3$—, R$_2$ is CH$_3$O—(CH$_2$)$_2$— and R$_4$ is CH$_3$—CO—O—CH$_2$— or (CH$_3$)$_2$N—CO—O—CH$_2$—; or g) R$_1$ is CH$_2$=CH—CH$_2$—, R$_2$ is

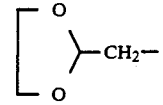

and R$_4$ is CH$_3$—CO—O—CH$_2$— or HO—CH$_2$—.

13. A compound according to claim 2, of formula I

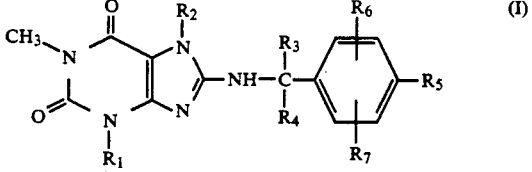 (I)

wherein

R$_1$ is methyl, allyl, or cyclopropylmethyl,

R$_2$ is (C$_{1-3}$hydroxyalkyl)methyl or (C$_{1-4}$alkoxy—C$_{1-3}$alkyl)methyl, C(R$_3$)R$_4$ is (R)—CH(CH$_2$OH), (R)—CH(CH$_2$OCH$_3$), or (R)—CH[CH$_2$O—CO—N(CH$_3$)$_2$], R$_5$ is methoxy, R$_6$ is hydrogen, and R$_7$ is (3)-methoxy, or a physiologically-hydrolysable and -acceptable carobxylic acid ester thereof.

* * * * *